United States Patent [19]

Fielden et al.

[11] Patent Number: 5,629,016
[45] Date of Patent: *May 13, 1997

[54] WATER-DISPERSIBLE TABLETS

[75] Inventors: Krystyna E. Fielden, Cheshunt; Michael J. D. Gamlen, Dartford, both of England

[73] Assignee: Glaxo Wellcome Inc., Research Triangle Park, N.C.

[*] Notice: The portion of the term of this patent subsequent to Oct. 3, 2014, has been disclaimed.

[21] Appl. No.: 99,099

[22] Filed: Jul. 29, 1993

Related U.S. Application Data

[63] Continuation-in-part of Ser. No. 41,126, Mar. 30, 1993, abandoned, which is a continuation of Ser. No. 827,655, Jan. 29, 1992, abandoned.

[30] Foreign Application Priority Data

Jan. 30, 1991 [GB] United Kingdom .................... 9102019

[51] Int. Cl.$^6$ .................................................. A61K 9/20
[52] U.S. Cl. .......................... 424/464; 424/465; 424/468; 424/469; 424/484
[58] Field of Search ...................... 424/484, 464, 424/465, 468, 469

[56] References Cited

U.S. PATENT DOCUMENTS

| | | | |
|---|---|---|---|
| 3,427,379 | 2/1969 | Barry et al. | 424/14 |
| 3,432,593 | 3/1969 | Shepard | 424/20 |
| 3,567,819 | 3/1971 | Leonia et al. | 424/16 |
| 4,072,535 | 2/1978 | Short et al. | 106/210 |
| 4,086,335 | 4/1978 | Bruscato et al. | 514/161 |
| 4,159,345 | 6/1979 | Takeo et al. | 514/781 |
| 4,209,513 | 6/1980 | Torode et al. | 514/158 |
| 4,251,518 | 2/1981 | Moore et al. | 514/54 |
| 4,304,773 | 12/1981 | Wong et al. | 514/223 |
| 4,305,502 | 12/1981 | Gregory et al. | 206/532 |
| 4,322,449 | 3/1982 | Voss et al. | 427/214 |
| 4,369,308 | 1/1983 | Trubiano | 536/106 |
| 4,371,516 | 2/1983 | Gregory et al. | 424/485 |
| 4,414,198 | 11/1983 | Michaelson | 424/44 |
| 4,517,179 | 5/1985 | Raghunathan | 514/249 |
| 4,600,579 | 7/1986 | Salpekar et al. | 424/80 |
| 4,602,017 | 7/1986 | Sawyer et al. | 514/242 |
| 4,631,305 | 12/1986 | Guyer et al. | 523/400 |
| 4,661,521 | 4/1987 | Salpekar et al. | 514/613 |
| 4,711,777 | 12/1987 | Tan et al. | 424/79 |
| 4,757,090 | 7/1988 | Salpekar et al. | 514/613 |
| 4,774,083 | 9/1988 | Tan et al. | 424/79 |
| 4,781,925 | 11/1988 | Michelucci et al. | 424/465 |
| 4,832,956 | 5/1989 | Gergely et al. | 424/466 |
| 4,837,031 | 6/1989 | Denton | 424/464 |
| 4,847,249 | 7/1989 | Sawyer et al. | 514/242 |
| 4,904,477 | 2/1990 | Ho et al. | 424/465 |
| 4,910,023 | 3/1990 | Botzolakis et al. | 423/470 |
| 4,925,676 | 5/1990 | Sellassie et al. | 424/470 |
| 4,927,639 | 5/1990 | Sellassie et al. | 424/497 |
| 4,950,484 | 8/1990 | Olthoff et al. | 424/464 |
| 4,965,072 | 10/1990 | Alexander et al. | 424/458 |
| 4,968,517 | 11/1990 | Gergely et al. | 426/285 |
| 4,970,078 | 11/1990 | Holinej | 424/465 |
| 4,999,200 | 3/1991 | Casillan | 424/480 |
| 5,006,345 | 4/1991 | Lang | 424/467 |
| 5,037,658 | 8/1991 | Urban et al. | 424/469 |
| 5,047,247 | 9/1991 | Milovac et al. | 424/465 |
| 5,049,586 | 9/1991 | Ortega et al. | 514/557 |
| 5,064,656 | 11/1991 | Gergely et al. | 424/463 |
| 5,069,910 | 12/1991 | Kovacie et al. | 424/464 |
| 5,073,377 | 12/1991 | Alexander et al. | 424/494 |
| 5,085,869 | 2/1992 | Olthoff et al. | 424/499 |
| 5,087,454 | 2/1992 | Duerholz et al. | 424/464 |
| 5,136,080 | 8/1992 | Miller et al. | 558/410 |

FOREIGN PATENT DOCUMENTS

| | | |
|---|---|---|
| 8906/91 | 6/1992 | Australia . |
| 0261595B1 | 3/1988 | European Pat. Off. . |
| 0294933 | 5/1988 | European Pat. Off. . |
| 0305843A2 | 3/1989 | European Pat. Off. . |
| 0350701 | 1/1990 | European Pat. Off. . |
| 0350701A2 | 1/1990 | European Pat. Off. . |
| 0372934A2 | 6/1990 | European Pat. Off. . |
| 0391851A1 | 10/1990 | European Pat. Off. . |
| 247892 | 4/1991 | European Pat. Off. . |
| 0459819A2 | 12/1991 | European Pat. Off. . |
| 0265226 | 5/1992 | European Pat. Off. . |
| 2016622 | 10/1971 | Germany . |
| 24078 | 10/1968 | Japan . |
| 207678 | 11/1986 | New Zealand . |

(List continued on next page.)

OTHER PUBLICATIONS

Wai, et al., "Applications of the Montmorillonites in Tablet Making," J. Pharm. Sci., 55: 1244–1248 (1966).
Wai & Banker, "Some Physicochemical Properties of the Montmoril–lonites," J. Pharm. Sci., 55: 1215–1220 (1966).
Granberg, et al., "The Use of Dried Bentonite as a Disintegrat–ing Agent in Compressed Tablets of Thyroid," J. Am. Pharm. Assoc. Sci., 43: 648–651 (1949).
Gross, et al., "A Comparative Study of Tablet Disintegrating Agents," J. Am. Pharm. Assoc. Sci., 41: 157–161 (1952).
Firouzabadian, et al., "Some Recently Developed Chemicals as Disintegrating Agents for Compressed Tablets," J. Am. Pharm. Assoc. Sci., 43: 248–250 (1954).
Ward, et al., "Evaluation of Tablet Disintegrants," Drug Cosmetic Ind. 91: 35–36, 92, 110–111 (1962).
Nair, et al., "Studies on Disintegration of Compressed Tablets I. Effect on Disintegration of the Procedure Used in Incorporating the Disintegrating Agent," J. Am. Pharm. Assoc. Sci., 46: 131–134 (1957).

(List continued on next page.)

Primary Examiner—Raj Bawa
Attorney, Agent, or Firm—Nixon & Vanderhye

[57] ABSTRACT

A water-dispersible tablet comprises acyclovir and a dispersing agent. The dispersing agent is a swellable clay such as a smectite e.g., Veegum F or bentonite, and is present within the granules of the tablet to provide a tablet which is capable of dispersing in water within 3 minutes to provide a dispersion which will pass through a 710 μm sieve. The tablet also includes a cellulostic excipient. The tablet can be optionally film-coated, in which case the dispersion time is less than 5 minutes.

22 Claims, No Drawings

FOREIGN PATENT DOCUMENTS

| | | |
|---|---|---|
| 222701 | 6/1990 | New Zealand . |
| 777516 | 6/1957 | United Kingdom . |
| 837451 | 6/1960 | United Kingdom . |
| 1317400 | 5/1973 | United Kingdom . |
| 1421964 | 1/1976 | United Kingdom . |
| 1443023 | 7/1976 | United Kingdom . |
| 1480188 | 7/1977 | United Kingdom . |
| 1480175 | 7/1977 | United Kingdom . |
| 1533243 | 11/1978 | United Kingdom . |
| 1546448 | 5/1979 | United Kingdom . |
| 1548022 | 7/1979 | United Kingdom . |
| 2033225 | 5/1980 | United Kingdom . |
| 1601833 | 11/1981 | United Kingdom . |
| 2086725 | 5/1982 | United Kingdom . |
| 2124078 | 2/1984 | United Kingdom . |
| 2157170 | 10/1985 | United Kingdom . |
| 2197197 | 5/1988 | United Kingdom . |
| 2249957A | 5/1992 | United Kingdom . |
| 83/00809 | 3/1983 | WIPO . |
| 87/05804 | 10/1987 | WIPO . |
| 91/03241 | 3/1991 | WIPO . |
| 91/07174 | 5/1991 | WIPO . |

OTHER PUBLICATIONS

Patel, et al., "Veegum as Binding Agent for Compressed Tablets," Indian J. Pharm., 19: 4–10 (1957).

Feinstein, et al., "Comparative Study of Selected Disintegrating Agents," J. Pharm. Sci. 55: 332–334 (1966).

Varley, A., "The Generic Inequivalence of Drugs," JAMA, 206: 1745–1748 (1968).

Delonca, et al., "Study of the Activity of Some Disintegrants as a Function of Procedure and of the Solubility of the Active Principles," J. Pharm. Belg. 26(4): 447–458 (1971) – English Translation.

Wagner, et al., "In Vivo and In Vitro Availability of Commercial Warfarin Tablets," J. Pharm. Sci. 60: 666–677 (1971).

McGinty, et al., "Optimization of Slow–Release Tablet Formulations Containing Montmorillonite I. Properties of Tablets," Drug Development and Industrial Pharmacy 6: 399–410 (1980).

Bargava, et al., "An Evaluation of Smecta as a Tablet Disintegrant and Dissolution Aid," Drug Development and Industrial Pharmacy 17: 2093–2102 (1991).

Barr, M., "In Pharmaceutical Systems . . . Clays as Dispersion Stabilizers," J. Amer. Pharm. Assoc. Sci. Ed. 46: 486–493.

US Pharmacopoeia, pp. 579, 1573, 1574, 1534 and 1535 (1985).

British Pharmacopoeia, pp. 27, 28, 51, 52, 62, 323–325 (1985).

Martindale, The Extra Pharmacopoeia, 29th Edition, pp. 4, 1077, 1092 and 1433.

The Handbook of Pharmaceutical Excipients, pp. 9–11, 150–152, 166–169.

Armstrong, N., "Tableting" from Pharmaceutics: The Science of Dosage Form Design, (Ed. Aulton): 647–668 (1988).

Rubinstein, M., "Tablets" from Pharmaceutics: The Science of Dosage Form Design, (Ed. Aulton): 304–321 (1988).

Rudnic, et al., "Oral Solid Dosage Forms," from Remington's Pharmaceutical Sciences (ed. Gennaro), pp. 1633–1665 (1990).

Disanto, A., "Bioavailability and Bioequivalency Testing," from Remington's Pharmaceutical Sciences (ed. Gennaro), pp. 1451–1458 (1990).

Banker, et al., "Tablets," from The Theory and Practice of Industrial Pharmacy, pp. 293–345.

Marshall, et al., "Tablet Dosage Forms," from Modern Pharmaceutics (eds., Banker, G. & Rhodes, C.) pp. 355–425 (1990).

Shangraw, R., "Specialty Tablet and Capsules," from Modern Pharmaceutics (eds. Banker, G. & Rhodes, C.) pp. 427–440 (1990).

Rudnic et al, Drug Development and industrial Pharmacy; 7(3), pp. 347–358; (1981).

Lowenthal, J. Pham Sci, vol. 61; No. 11, Nov. 1972, pp. 1695–1711.

Holstius et al.; J. Amer. Pharm, Sci (1952), 41,505.

Patel et al., Indian J. Pharm., 26,313 (1964).

Patel, et al., Indian J. Pharm., 28,244 (1966).

Smeczi, et al. Acta Pharm. Hungary., 40,124 (1970).

Billups et al., Amer J. Pharm. 136, 25 (1964).

Patel, et al., Indian J. Pharm., 25,220 (1963).

Salo et al, Pharmzhl, 20,5 (1965)—Int. Pharm Abst 3, 1342d (1966).

Birmancevic et al, Arh. Farm. (1981), 31 (1–2), 45–54.

Birmancevic et al., Acta, Pharmaceutica Jugoslavia (1974), 24, pp. 237–240.

Birmancevic et al. Arch. Farm (1978), 28, 21–28.

Borzonuv et al., Chem Abstr., 69 1097q (1968).

Borzonuv et al., Chem Abst., 71 3385y (1969).

Schmeczi, et al. Chem Abst. 70, 14395q (1969).

Saufiulin, et al., Chem Abst. 58, 13727a (1963).

Kuever et al., J. American Pharm. Ass. Sci, 17,365 (1928).

Shotton et al. J. Pharm Pharmac., 1972 24, 798–803.

WATER-DISPERSIBLE TABLETS

This application is a continuation-in-part of U.S. Ser. No. 041,126 filed Mar. 30, 1993, now abandoned, which is a continuation of U.S. Ser. No. 827,655 filed Jan. 29, 1992 (now abandoned).

The present invention relates to a water-dispersible tablet formulation containing acyclovir.

BACKGROUND OF THE INVENTION

Acyclovir (UK Patent Specification No. 1523865; U.S. Pat. No. 4,199,574) is a compound which has been found to have potent activity against viruses of the herpes family, particularly herpes simplex and herpes varicella zoster. Such activity has been demonstrated by the outstanding success of acyclovir in the therapeutic treatment of clinical conditions such as genital herpes caused by the herpes simplex virus, or chicken pox or shingles, caused by the varicella zoster virus.

In the treatment of certain conditions, it may be necessary to administer acyclovir to the patient in relatively large dosages to achieve the effective therapeutic levels of drug in the plasma, particularly when oral administration is desired. For example, in the treatment of shingles, it is recommended to administer acyclovir at a dosage regime of 800 mg five times per day. A tablet formulation containing 800 mg of acyclovir is currently available but its relatively large size sometimes renders it difficult to swallow by elderly patients, such patients being particularly susceptible to shingles.

We have now been able to prepare water-dispersible tablets containing acyclovir which can readily be dispersed in water to form a dispersion which can easily and conveniently be drunk by e.g. an elderly patient. More particularly the tablets of the invention meet the criteria for dispersible tablets set out in the British Pharmacopoeia (B.P. 1988, page 895, volume II) in that they disperse in water within 3 minutes to form a dispersion that will pass through a 710 μm sieve.

Furthermore, at a high drug loading, the overall size of a tablet containing 800 mg acyclovir (for shingles) is still small enough to swallow. The patient, depending on his capability, thus has the choice of swallowing or dispersing the tablet.

SUMMARY OF THE INVENTION

According to the present invention a water-dispersible tablet having 200 to 800 mg acyclovir, preferably about 200 mg, or about 400 mg, or about 800 mg acyclovir, is provided as follows:

| intragranular: | |
|---|---|
| Acyclovir | 65% w/w to 95% w/w, preferably 70% w/w to 90% w/w, more preferably 75 to 85% w/w, most preferably about 80% w/w |
| Povidone (e.g. Povidone K30) | 0.25% w/w to 5% w/w, preferably 0.5 w/w to 2% w/w |
| Swellable clay(s) | 0.5% w/w to 30% w/w, preferably 0.5% w/w to 10% w/w |
| excipient selected from substituted hydroxyalkyl cellulostic disintegrating agent preferably substituted hydroxypropyl cellulose (e.g. LHPC) and hydroxypropymethyl cellulose (e.g. LHPMC), or | 1% w/w to 25% w/w, preferably 1% w/w to 15% w/w such as 1% to 8% w/w, (e.g. 1% to 5% w/w) |
| Sodium starch glycollate (e.g. explotab and primojel): or a combination of said excipients | 1% w/w to 8% w/w, preferably 2% to 6% w/w |
| extragranular: | |
| Lubricant, | |
| The tablet can be optionally film coated, suitably using: | |
| Opadry | 0.1% w/w to 2% w/w, preferably 0.25% to 1.0% w/w |
| Polyethylene glycol 8000 | 0.1% w/w to 0.5% w/w, preferably 0.1% to 0.2% w/w |

In a further aspect of the present invention a water-dispersible tablet having 200 to 800 mg acyclovir, preferably about 200 mg, or about 400 mg, or about 800 mg acyclovir, is provided as follows:

| intragranular: | |
|---|---|
| Acyclovir | 65% w/w to 95% w/w, preferably 70% w/w to 90% w/w, more preferably 75% to 85% w/w, most preferably about 80% w/w |
| Povidone (e.g. Povidone K30) | 0.25% w/w to 5% w/w, preferably 0.5% to 2% w/w |
| Swellable clay selected from sepiolite such as attapulgite, or | 0.5% w/w to 30% w/w, preferably 0.5% w/w to 10% w/w, more preferably 3% to 10% w/w, still more |

| | |
|---|---|
| selected from smectite wherein the smectite is preferably montmorillonite, such as magnesium aluminium silicate (e.g. Veegum F) or bentonite; or a combination thereof | preferably about 5% w/w |
| Cellulostic excipient selected from microcrystalline cellulose (e.g. Avicel) substituted hydroxypropyl cellulose e.g. low substituted hydroxypropyl cellulose (LHPC) and substituted hydroxypropymethyl cellulose (e.g. LHPMC) e.g. low substituted hydroxypropylmethyl cellulose (LHPMC); or a combination thereof | 5% w/w to 25% w/w, preferably 5% to 15% w/w |
| Sodium starch glycollate (e.g. explotab and primojel) | 1% w/w to 8% w/w, preferably 2% w/w to 6% w/w |
| extragranular: | |
| lubricant, preferably magnesium stearate | 0.25% w/w to 2% w/w, preferably 0.25% to 1.0% w/w |
| The tablet can be optionally film coated, suitably using: | |
| Opadry | 0.1% w/w to 2% w/w, preferably 0.25% to 1.0% w/w |
| Polyethylene glycol 8000 | 0.1% w/w to 0.5% w/w, preferably 0.1% to 0.2% w/w |

In yet a further aspect of the present invention a water-dispersible tablet having 200 to 800 mg acyclovir, preferably about 200 mg or about 400 mg or about 800 mg acyclovir, is provided as follows:

| | |
|---|---|
| intragranular: | |
| Acyclovir | 65% w/w to 95% w/w, preferably 70% w/w to 90% w/w, more preferably 75% w/w to 85% w/w, most preferably about 80% w/w |
| Povidone (Povidone K30) | 0.25% w/w to 5% w/w, preferably 0.5% to 2% w/w |
| Swellable clay selected from sepiolite such as attapulgite, or selected from smectite wherein the smectite is preferably montmorillonite, such as magnesium aluminium silicate (e.g. Veegum F) or bentonite; or a combination thereof | 0.5% w/w to 30% w/w, preferably 0.5 w/w to 10% w/w, more preferably 3% to 10% w/w, still more preferably about 5% w/w |
| substituted hydroxypropyl cellulose (e.g. LHPC) or substituted hydroxypropymethyl cellulose (e.g. LHPMC); or a combination thereof | 1% w/w to 25% w/w, preferably 1% to 15% w/w such as 1% to 8% w/w (e.g. 1% to 5% w/w) |
| (optionally) microcrystalline cellulose (e.g. Avicel) | 5% to 25% w/w preferably 5% to 15% w/w |
| extragranular: | |
| lubricant, preferably magnesium stearate | 0.25% w/w to 2% w/w, preferably 0.25% to 1.0% w/w |
| The tablet can be optionally film coated, suitably using: | |
| Opadry | 0.1% w/w to 2% w/w, preferably 0.25–1.0% w/w |
| Polyethylene glycol 8000 | 0.1% w/w to 0.5% w/w, preferably 0.1–0.2% w/w |

In yet a further aspect of the present invention a water dispersible tablet having 200 to 800 mg acyclovir, preferably about 200 mg, or about 400 mg or about 800 mg acyclovir, is provided as follows:

| intragranular: | |
|---|---|
| Acyclovir | 65% w/w to 95% w/w, preferably 70% w/w to 90% w/w, more preferably 75% to 85% w/w, most preferably about 80% w/w |
| Povidone (e.g. Povidone K30) | 0.25% w/w to 5% w/w, preferably 0.5% to 2% w/w |
| Swellable clay preferably selected from sepiolite such as attapulgite, or selected from smectite wherein the smectite is preferably montmorillonite, such as magnesium aluminium silicate (e.g. Veegum F) or bentonite; or a combination thereof | 0.5% w/w to 30% w/w, preferably 0.5% to 10% w/w, more preferably 3% to 10% w/w, still more preferably about 5% w/w |
| substituted hydroxypropymethyl cellulose (e.g. LHPMC) (optionally) | 1% w/w to 25% w/w, preferably 1% to 15% w/w such as 1% to 8% (e.g. 1% to 5% w/w) |
| Sodium starch glycollate (e.g. explotab and primojel) (optionally) | 1% w/w to 8% w/w preferably 2% w/w to 6% w/w |
| microcrystalline cellulose (e.g. Avicel) | 5% w/w to 25% w/w, preferably 5% to 15% w/w |
| extragranular: | |
| lubricant, preferably Magnesium stearate | 0.25% w/w to 2% w/w, preferably 0.25% to 1.0% w/w |

The tablet can be optionally film coated, suitably using:

| | |
|---|---|
| Opadry | 0.1% w/w to 2% w/w, preferably 0.25% to 1.0% w/w |
| Polyethylene glycol 8000 | 0.1% w/w to 0.5% w/w, preferably 0.1% to 0.2% w/w |

Preferably acyclovir is present in a ⅔ hydrate form (i.e. a ratio 3 acyclovir:2 water molecules).

Yet a further aspect of the invention is granules for a water dispersible tablet as defined herein.

Preferably the dispersion time of a tablet according to the invention is less than 2 minutes, more preferably less than 1.50 minutes and most preferably less than 1 minute.

A further advantage of the tablets according to invention is that because a relatively fine dispersion is formed the tablet may have a lower dissolution time and thus the drug may be absorbed into the blood stream much faster. Furthermore the fast dispersion times and relatively fine dispersions obtained with tablets according to the invention are also advantageous for swallowable tablets. Thus tablets according to the invention can be presented both for dispersion in water and also for directly swallowing. Those tablets according to the invention that are intended for swallowing are preferably film-coated to aid swallowing. Such film-coating however increases the dispersion time up to 5 minutes determined in accordance with the above-mentioned B.P. test as required for disintegration of film-coated tablets. According to a further feature of the present invention therefore we provide a water-dispersible film-coated tablet wherein the dispersion time can be up to 5 minutes.

The particle size distribution of the dispersion is set out in the following table with the increasingly preferred values being quoted form left to right.

| Particle Size (μm)* | BP Standard | Preferably | More Preferably | Most Preferably |
|---|---|---|---|---|
| <710 | <100% | 100% | 100% | 100% |
| <300 | — | >50% | >70% | >80% |
| <200 | — | — | >50% | >70% |
| <150 | — | — | — | >50% |

*(equivalent spherical volume diameter)

The term "swellable clay" as used herein includes layered clays (such as smectites), porous fibrous clay minerals, and synthetic clay materials related in structure to layered clays and porous fibrous clays.

The term "layered clays" as used herein includes substantially homogeneous layered clays and mixtures thereof, and interstratified or mixed layered clays. Substantially homogeneous layered clays includes the smectite group for example dioctahedral and trioctahedral types. Examples of dioctahedral smectites are the montmorillonite group (montmorillonoids); magnesium and other (e.g. calcium) aluminium silicates such as Veegum in its various grades (e.g. Veegum, Veegum HV, Veegum F. and Veegum WG); almasilate; fullers earth (e.g. Surrey finest); American fullers earth; bentonite; beidellite; cheto montmorillonite, Wyoming montmorillonite, Utah montmorillonite; Tatalia and Chambers montmorillonites; and iron rich smectites such as nontrite (e.g. Garfield nontronite) and ferrian smectites.

Examples of triocatahedral smectites (also known as saponites) are Swinefordite, hectorite, stevensite. Examples of smectites containing more unusual elements are Volkhonsite, Medmontite, Sauconite, nickel smectites and vanadium smectites. As well as the montmorillonite group, related smectites such as vermiculites may also have application.

The term "interstratified or mixed layer clays", as used herein includes clays involving different layers arranged in a regular or irregular structure. The most common examples of such clays have generally two components in substantially equal proportions and have been given mineral names such as rectorite (mica-smectite), hydrobiotite (biotite-vermiculite), corrensiten (chlorite-smectite) allettite (talc-saponite). More irregular arrangements include illite-smectite, chlorite-smectite, and kaolinite-smectite. Further examples of interstratified clays are tosudite, tarasovite, allevardite, Japanese bentonite ("acid clays"), AWAZU acid clay, and kaolinite-smectite. Other mixed layer clays may include one or more of the following minerals; clinchlore, chamosite, nimite, thuringite, sudoite, and cookeite. Mixed layer smectites are also known e.g. interdispersed montmorillonite and beidellite layers. The layers of mixed layer clays may be homogeneous or non-homogeneous.

The term "porous fibrous clays" includes polygorskite and sepiolite such as, for example attapulgite and American fuller's earth.

The term "synthetic clay materials" as used herein includes materials related in structure to layered clays and porous fibrous clays such as synthetic hectorite (lithium magnesium sodium silicate) for example laponite®.

It will be appreciated that within the scope of the invention the following classes of clays have application alone or in combination with one another and in mixed layer clays: kaolinites, serpentines, pyrophyllites, talc, micas and brittle micas, chlorites, smectites and vermiculites, palygorskites and sepiolites. Other phyllosilicates (clay minerals) which may be employed in the tablets according to the invention are allophane and imogolite.

The following references describe the characterisation of clays of the above type: Chemistry of Clay and Clay Minerals. Edited by A. C. D. Newman. Mineralogical Society Monograph No. 6, 1987, Chapter 1; S. W. Bailey; Summary of recommendations of AIPEA Nomenclature Committee, Clay Minerals 15, 85–93; and A Handbook of Determinative Methods in Mineralogy, 1987, Chapter 1 by P. L. Hall.

Suitably the swellable clay is a pharmaceutically acceptable crystalline mineral clay having a lattice structure which expands upon hydration, preferably a pharmaceutically acceptable smectite or attapulgite clay, especially a montmorillonoid, more preferably yet a montmorillonoid chosen from the group consisting of montmorillonite, sauconite, vermiculite, bentonite and hectorite, still more preferably an aluminium magnesium silicate (also termed magnesium aluminum silicates) and most preferably Veegum® (e.g. Veegum F) Veegum® is a complex colloidal magnesium aluminium silicate described and characterised in Technical Booklet No. 97, R. T. Vanderbilt Company, Inc., Industrial Minerals and Chemicals, 30 Winfield Street, Norwalk, Conn. 06855, U.S.A: an especially preferred such material is Veegum F (loc. cit.).

The term "smectite" as used herein in relation to tablets of the present invention includes the smectites as exemplified herein and with reference to O'Brian P. and Williamson C. J., in "Clays and Clay Minerals vol. 38 No. 3 pp322–326, 1990" and the other clay nomenclature references set out hereinbefore.

The term "magnesium aluminium silicate" as used herein in relation to tablets of the present invention should be understood to include the Aluminium Magnesium Silicate defined in the *British Pharmacopoeia*, volume 1, pages 27–28, 1988 and the Magnesium Aluminium Silicate defined in the *United States Pharmacopoeia, National Formulary XVI*, pages 1943–1944, 1990. Advantageously, said silicate is in the form of a microfine powder having a No. 325 US Standard mesh particle size, a viscosity of 250 cps (±25%) for a 5.5% (w/v) aqueous dispersion and an acid demand (the volume in ml. of 0.1N hydrochloric acid required to reduce the pH of one gram to 4) of 6–8: such a material is available as VEEGUM F (R. T. Vanderbilt CO., New York, N.Y., U.S.A.; K & K-Greeff Chemicals Ltd., Croydon, Surrey CR9 3QL, England).

The amount of swellable clay employed in the tablet according to the invention generally depends on the weight of the tablet.

For a dispersible tablet according to the present invention, the intra-granular amount of swellable clay such as a crystalline mineral clay for example, magnesium aluminium silicate is suitably present in the following general ranges 0.5 to 30% w/w, more preferably 0.5 to 10% w/w, still more preferably 3 to 10% w/w, and most preferably 5 to 10%, most desirably about 5% w/w.

The tablets according to the invention will generally contain a pre-determined amount of acyclovir depending on the desired dosage and the total weight of the tablet.

The tablets generally contain 200 to 800 mg, such about 200 mg, about 400 mg and about 800 mg of acyclovir. Such dosage units may be administered one or more times, for example up to five times, per day, at the discretion of the physician, according to the age and condition of the patient and the particular condition being treated. For an acyclovir tablet having a total weight about 1000 to 1200 mg and containing about 750 to 850 mg of acyclovir, the swellable clay e.g. Veegum F, is preferably present in an amount of 40 to 120 mg intragranularly.

In general the tablets according to the invention contain 65 to 95% w/w preferably 70–90% w/w, preferably 75 to 85% w/w and most preferably about 80% w/w of acyclovir.

There are presently on the markets tablets containing an equivalent (unfactorized amount) of about 200 mg, about 400 mg and about 800 mg of acyclovir which is equivalent to about 80% w/w of the tablet.

Preliminary experimentation suggests that when acyclovir is present in an amount of at least 65% w/w in tablets according to the invention, the dispersion time remains substantially constant over a range of tablet hardnesses. This is a considerable quality control advantage since in industrial manufacture it is essential to maintain a constant tablet hardness. Tablets according to the invention can thus be produced with sufficient hardness and friability so that they can easily be film-coated. A tablet according to the invention should desirably have a friability of about 2% or less, preferably 0.5% or less.

Based on experiments that we have carried out, it has been found that in addition to the amount of swellable clay present within the granules of the tablet, a further amount of swellable clay may be present outside the granules. At very low intra-granular amounts (such as 1% w/w or below), higher extra-granular amounts (such as about 10% w/w or more) may decrease the dispersion time, but in general extra-granular addition has little or no effect on the dispersion time. The maximum percentage(s) of the clay present within the granules and, optionally outside the granules, may be limited by other practical considerations such as poor flow and compression properties.

Excipients suitable for inclusion in the tablets according to the invention include the following:

a) Lubricants: examples of lubricants with percentage weights which are suitable for a tablet are: stearates (e.g. magnesium or calcium stearate) 0.2 to 5% w/w, preferably 0.25 to 1% w/w, talc 0.19 to 5% w/w, preferably 1 to 2% w/w, polyethylene glycol 0.19 to 5% w/w, preferably 2 to 5% w/w, liquid paraffin 0.18 to 5% w/w, preferably 2 to 5% w/w, sodium lauryl sulphate 0.19% to 5% w/w, preferably 0.5 to 2% w/w, magnesium lauryl sulphate 0.12 to 5% w/w, preferably 1 to 2% w/w, colloidal silicon dioxide 0.1 to 5% w/w, preferably 0.1 to 1.0% w/w, palmitostearate 0.01 to 5% w/w, preferably 1 to 3% w/w, stearic acid 0.01 to 5% w/w, preferably 1 to 3% w/w, zinc stearate 0.01 to 2% w/w, 0.5 to 1.5% w/w, hydrogenated vegetable oil 0.5 to 5% w/w, preferably 1 to 3% w/w. More suitably the lower value is 0.25%.

b) Wetting agents/surfactants: examples with suitable amounts are: sodium dodecyl sulphate 0 to 10% w/w, preferably 0.5 to 2% w/w, sodium lauryl sulphate 0 to 10% w/w, preferably 0.1 to 3.0% w/w polyoxyethylene sorbitan fatty acid esters (Tweens) 0 to 3% w/w, preferably 0.05 to 1.0% w/w, polyoxyethylene stearates 0 to 2% w/w, preferably 0.05 to 1.0% w/w, sorbitan fatty acid esters (Spans) 0 to 3% w/w; preferably 0.05 to 1.0% w/w.

c) Glidants: for example, talc 0 to 5% w/w, preferably 1 to 2% w/w, starch 0 to 15% w/w, preferably 2 to 10% w/w, magnesium stearate up to 5%, preferably 0–2.0% w/w, silica derivatives generally 0 to 1% w/w, preferably 0.2 to 0.5% w/w, such as colloidal silica (e.g. Aerosil) 0 to 0–5% w/w, preferably 0.25 to 3% w/w, pyrogenic silica 0 to 2% w/w, preferably 0.25 to 1% w/w, hydrated sodium silicoaluminate 0 to 2% w/w, preferably 0.5 to 1% w/w, colloidal silicon dioxide 0 to 0.5% w/w.

d) Flavouring agents: are used in for example approximate quantities of 0 to 5% w/w, preferably 0.25 to 2% w/w, orange, cherry and strawberry, raspberry, grape and passion fruit.

e) Sweetening agents: for example sodium saccharin 0 to 10% w/w, preferably, 0.5 to 5.0% w/w, aspartame 0 to 10% w/w, preferably 0.25 to 5.0% w/w, confectioners sugar 0 to 30% w/w, preferably 5 to 20% w/w, sorbitol 25 to 90% w/w, preferably 0.5 to 10% w/w, sucrose 0 to 85% w/w, preferably 0.5 to 20% w/w, xylitol 0–20% w/w, preferably 0.5 to 10% w/w.

Such materials may be incorporated at the appropriate stage(s) of the manufacturing process together with any other agents (e.g. colourants).

A process for the preparation of a water-dispersible tablet according to the invention comprises the steps of:

a) admixing in dry finely divided form 200 to 800 mg e.g. about 200 mg or about 400 mg or about 800 mg acyclovir (65 to 95% w/w), 0.25 to 5% w/w povidone optionally dissolved in a pharmaceutically acceptable liquid, 0.5 to 30% w/w of a swellable clay, an excipient selected from the group consisting of 5 to 25% w/w substituted hydroxyalkyl cellulostic disintegrating agent and 1 to 8% w/w sodium starch glycollate, or a combination thereof;

b) addition of a quantity of a pharmaceutically acceptable liquid sufficient to moisten the dry mixture;

c) granulation of the resulting moist mixture to form granules;

d) drying the granules and blending the granules with a lubricant; and e) compression of the granules to form a tablet Suitably the dry mixing is effected with a mixing time of 5 minutes to 25 minutes preferably about 10 minutes.

The swellable clay can be dry mixed with acyclovir and other excipients and then granulating solution added, or the clay and other excipients can be dispersed firstly in the granulating solution and then added to the acyclovir and any other excipients prior to granulation.

The liquid employed to moisten the dry mixture, prior to the granulation step, is preferably aqueous, for example water or a mixture of water and a suitable alcohol such as ethanol or isopropanol.

Wet mixing or granulating times which are suitable (depending on the type of mixer used) are 5 to 20 minutes.

Suitable granule drying times and conditions (which will vary according to the type of equipment used and batch size of granules) are about 50° to 80° C., (using a dryer such as with a tray or fluid bed dryer) to obtain a moisture content generally below about 4%.

The tablets may optionally be film-coated, for example with hydroxypropylmethyl cellulose, polyethylene glycol or titanium dioxide, and/or may be scored and/or may be polished, for example with polyethylene glycol 8000. If the tablets are film-coated, this makes them easier to swallow or chew (i.e. the tablets are suitable for either dispersion in water or for direct swallowing or chewing), but the dispersion time is increased.

The above-mentioned test for dispersion time is carried out using the following apparatus and method, which is extracted from the British Pharmacopoeia 1988, page 895, volume II.

Apparatus (a) A rigid basket-rack assembly supporting six cylindrical glass tubes 75.0 to 80.0 mm long, 21.5 mm in internal diameter and with a wall thickness of about 2 mm.

(b) A cylindrical disc for each tube, each 20.55 to 20.85 mm in diameter and 9.35 to 9.65 mm thick, made of transparent plastic with a relative density of 1.18 to 1.20, pierced with five holes, each 2 mm in diameter, one in the centre and the other four spaced equally on a circle of radius 6 mm from the centre of the disc. Four equally spaced grooves are cut in the lateral surface of the disc in such a way that at the upper surface of the disc they are 9.5 mm wide and 2.55 mm deep and at the lower surface 1.6 mm square.

(c) The tubes are held vertically by two superimposed transparent plastic plates 90 mm in diameter and 6 mm thick, perforated by six holes having the same diameter as the tubes. The holes are equidistant from the centre of the plate and are equally spaced from one another. Attached to the underside of the lower plate is a piece of woven gauze made from stainless steel wire 0.635 mm in diameter and having nominal mesh apertures of 2.00 mm.

(d) The plates are held rigidly in position and 77.5 mm apart by vertical metal rods at the periphery and a metal rod is also fixed to the centre of the upper plate to enable the assembly to be attached to a mechanical device capable of raising and lowering it smoothly through a distance of 50 to 60 mm at a constant frequency of between 28 and 32 cycles per minute.

(e) The assembly is suspended in the liquid medium in a suitable vessel, preferably a 1000-ml beaker. The volume of liquid is such that when the assembly is in the highest position the wire mesh is at least 15 mm below the surface of the liquid and when the assembly is in the lowest position the wire mesh is at least 25 mm above the bottom of the beaker and the upper open ends of the tubes remain above the surface of the liquid.

(f) A suitable device maintains the temperature of the liquid at 19° C. to 21° C.

The design of the basket-rack assembly may be varied provided that the specifications for the glass tubes and wire mesh are maintained.

Method

Introduce one tablet into each tube, optionally adding a disc to each tube. Suspend the assembly in the beaker containing the specified liquid and operate the apparatus for a maximum period of three minutes. Remove the assembly from the liquid. The tablets pass the test if all six have dispersed within a period of three minutes, five minutes for film-coated tablets.

The test for dispersion quality (i.e. uniformity of dispersion) is carried out as follows:

Place two tablets in 100 ml of water and stir until completely dispersed. A smooth dispersion is produced which passes through a sieve screen with a nominal mesh aperture of 710 μm.

The references herein to tablets according to the invention include both film-coated and non-film-coated tablets.

After the dispersion has passed through the 710 μm mesh screen, there should be substantially no residue, except fragments of undissolved tablet coating or shell, remaining on the screen or adhering to the lower surface of the disc, if a disc optionally has been used; and if any residue remains, it should consist of a soft mass having no palpably firm, unmoistened core.

Generally suitable compression weights and final table hardness will vary according to the size of tablet, but generally suitable values are as follows:

| Approximate Tablet weight (mg) | Approximate Tablet diameter (mm) | Approximate Target tablet hardness (Kp) |
|---|---|---|
| 60 | 5.6 | 1–2 |
| 80 | 6.4 | 3–4 |
| 125 | 7.4 | 4–5 |
| 250 | 8.6 | 5–6 |
| 330 | 9.4 | 6–8 |
| 500 | 11.0 | 10–12 |
| 600 | 11.8 | 10–14 |
| 1000 | 14.0 | 12–16 |

DESCRIPTION OF THE PREFERRED EMBODIMENTS

The following Examples illustrate the present invention.

Examples 1 to 6 and 29 are comparative examples while examples 7–28, 30 to 33 describe the preparation of tablets according to the invention

| Example Number | 1 mg/tablet | 2 mg/tablet | 3 mg/tablet | 4 mg/tablet |
|---|---|---|---|---|
| Intra-granular: | | | | |
| Acyclovir* | 848.0 | 848.0 | 844.0 | 844.0 |
| Avicel PH101 | 60.0 | NIL | 101 | NIL |
| Lactose | 120.0 | NIL | NIL | NIL |
| Starch (maize) | NIL | NIL | 50 | NIL |
| Explotab | NIL | 75.0 | 50 | NIL |
| Primogel | NIL | NIL | NIL | 75.0 |
| Ac-Di-Sol | 83.0 | NIL | 23 | NIL |
| Kollidon CL | NIL | NIL | NIL | NIL |
| Saccharin sodium | 20.0 | 10.0 | NIL | NIL |
| Sodium lauryl sulphate | 5.0 | NIL | 3.0 | NIL |
| Sodium docusate | NIL | 1.0 | NIL | 0.5 |
| Dicalc. phosph. dihyr. | NIL | NIL | NIL | 200.0 |
| Povidone K30 | NIL | 10.0 | 22 | 11.2 |
| Extra-granular: | | | | |
| Ac-Di-Sol | 40.0 | NIL | NIL | NIL |
| Avicel PH102 | 60.0 | 94 | NIL | NIL |
| Amberlite IRP88 | NIL | NIL | NIL | 50.0 |
| Kollidon CL | NIL | NIL | 60.1 | NIL |
| Mg stearate | 12.0 | 10.0 | 10.1 | 11.0 |
| Tablet weight (mg) | 1248.0 | 1048.0 | 1163.2 | 1191.7 |

*In the following examples 13, 14 and 15, the actual quantity of acyclovir used is calculated from a factor so as to provide 800 mg of acyclovir per tablet. (The factor for acyclovir is typically 105.5 equivalent to 100 acyclovir). In examples 13, 14 and 15, the actual quantity of acyclovir used was adjusted from the factor so as to provide 800 mg of acyclovir per tablet.

-continued

| Example Number | 5 mg/tablet | 6 mg/tablet | 7 mg/tablet | 8* mg/tablet | 9 mg/tablet |
|---|---|---|---|---|---|
| Acyclovir | 844.0 | 848.0 | 844.0 | 848.0 | 848.0 |
| Avicel PH101 | 101.0 | 83.46 | 100.0 | 89.0 | 89.0 |
| Veegum F | NIL | NIL | 53.0 | 53.0 | 53.0 |
| Sodium starch glycollate (Explotab) | 90.0 | 39.37 | 42.0 | 42.0 | 42.0 |
| Povidone K30 | 11.0 | 10.27 | NIL | 11.0 | 11.0 |
| Magnesium stearate | 9.5 | 8.85 | 9.4 | 9.4 | 9.4 |
| Film coat composite 1: Opadry | NIL | NIL | NIL | NIL | 7.86 |
| Film coat composite 2: Polyethylene glycol 8000 | NIL | NIL | NIL | NIL | 2.097 |
| Tablet weight (mg) | 1055.5 | 989.95 | 1048.4 | 1052.4 | 1062.4 |

*Tablets containing either a 200 mg or 400 mg (unfactorized) dose of acyclovir were also made using the granule of Example 8, with the following compression weights:
200 mg acyclovir tablet: 263.1 mg
400 mg acyclovir tablet: 526.2 mg In accordance with the invention, to illustrate that the disintegration time remains substantially constant at different tablet hardnesses, the formulation of Example 7 was compressed at approximately 8 kp (7a), 12 kp (7b) and 18 kp (7c) and the results noted hereafter.

| Example Number | 10 mg/tablet | 11 mg/tablet | 12 mg/tablet |
|---|---|---|---|
| Acyclovir | 848.0 | 848.0 | 848.00 |
| Avicel PH 101 | 118.5 | 71.1 | 86.8 |
| Veegum F | 26.5* | 53.0 | 53.0 |
| Primojel | 42.0 | 42.0 | 42.0 |
| Povidone K30 | NIL | 20.9 | 5.2 |
| Magnesium stearate | 9.4 | 9.4 | 9.4 |
| Tablet weight (mg) | 1044.4 | 1044.4 | 1044.4 |

*Veegum added as a paste-example contains no PVP-K30 as a binder.

| Examples of Acyclovir formulations | | | |
|---|---|---|---|
| Example Number | 13 mg/tablet | 14 mg/tablet | 15 mg/tablet |
| Component (mg/tablet) | | | |
| Acyclovir | 800.0 | 800.0 | 800.0 |
| Avicel PH 101 | 100.0 | 89.0 | 89.0 |
| Veegum F | 53.0 | 53.0 | 110.0 |
| Sodium starch glycollate | 42.0 | 42.0 | 42.0 |
| Povidone K30 | NIL | 11.0 | 11.0 |
| Magnesium stearate | 9.4 | 9.4 | 9.9 |
| Tablet weight (mg) | 1004.4 | 1004.4 | 1061.9 |

| Example Number | 16 % w/w | 16 mg/tablet | 17 % w/w | 17 mg/tablet | 18 % w/w | 18 mg/tablet | 19 % w/w | 19 mg/tablet |
|---|---|---|---|---|---|---|---|---|
| Acyclovir | 79.95 | 848.0 | 75.54 | 795.00 | 65.47 | 689.00 | 55.00 | 583.00 |
| Avicel PH 101 | 8.86 | 89.0 | 8.86 | 89.00 | 8.86 | 89.00 | 8.86 | 89.00 |
| Veegum F | 5.28 | 53.0 | 10.00 | 106.00 | 20.00 | 212.00 | 30.00 | 318.00 |
| Explotab | 4.18 | 42.0 | 4.18 | 42.00 | 41.8 | 42.00 | 4.18 | 42.00 |
| Povidone K30 | 1.09 | 11.0 | 1.09 | 11.00 | 1.09 | 11.00 | 1.09 | 11.00 |

Examples of Acyclovir formulations

| | | | | | | | | |
|---|---|---|---|---|---|---|---|---|
| Magnesium stearate | 0.94 | 9.4 | 0.94 | 9.40 | 0.94 | 9.40 | 0.94 | 9.40 |
| Tablet weight (mg) | 100.0 | 1052.4 | 100.0 | 1052.4 | 100.0 | 1052.4 | 100.0 | 1052.4 |

| Example Number | 20 % w/w | 20 mg/tablet | 21 % w/w | 21 mg/tablet | 22 % w/w | 22 mg/tablet |
|---|---|---|---|---|---|---|
| Acyclovir | 45.32 | 477.00 | 84.3 | 890.00 | 44.93 | 39848.00 |
| Avicel PH 101 | 8.86 | 89.00 | 8.86 | 89.00 | 8.86 | 157.76 |
| Veegum F | 40.00 | 424.00 | 1.00 | 10.60 | 40.00 | 712.22 |
| Explotab | 4.18 | 42.00 | 4.18 | 42.00 | 4.18 | 74.43 |
| Povidone K30 | 1.09 | 11.00 | 1.09 | 11.00 | 1.09 | 19.41 |
| Magnesium stearate | 0.94 | 9.40 | 0.94 | 9.40 | 0.94 | 16.74 |
| Tablet weight (mg) | 100.00 | 1052.4 | 100.00 | 1052.4 | 100.00 | 1828.56 |

| Example Number | 23 % w/w | 23 mg/tablet | 24 % w/w | 24 mg/tablet | 25 % w/w | 25 mg/tablet | 26 % w/w | 26 mg/tablet |
|---|---|---|---|---|---|---|---|---|
| Acyclovir | 65.47 | 689.00 | 55.00 | 583.00 | 45.32 | 477.00 | 79.65 | 848.00 |
| Avicel PH 101 | 8.86 | 89.00 | 8.86 | 89.00 | 8.86 | 89.00 | 8.86 | 89.0 |
| Veegum F | *20.00 | (106.00 (106.00 | *30.00 | (159.00 (159.00 | *40.00 | (212.00 (212.00 | 5.28 | 53.0 |
| Explotab | 4.18 | 42.00 | 4.18 | 42.00 | 4.18 | 42.00 | 4.18 | 42.0 |
| Povidone K30 | 1.09 | 11.00 | 1.09 | 11.00 | 1.09 | 11.00 | 1.09 | 11.0 |
| Magnesium stearate | 0.94 | 9.40 | 0.94 | 9.40 | 0.94 | 9.40 | 0.94 | 9.4 |
| Tablet weight (mg) | 100.00 | 1052.4 | 100.00 | 1052.4 | 100.00 | 1052.4 | 100.00 | 1052.4 |

*In these examples the Veegum is distributed equally both intra-granularly and extra-granularly.

| Example Number | 27 % w/w | 27 mg/tablet | 28 % w/w | 28 mg/tablet | 29 % w/w | 29 mg/tablet | 30 mg/tablet | 31 mg/tablet |
|---|---|---|---|---|---|---|---|---|
| Acyclovir | 84.43 | 848.00 | 84.68 | 848.00 | 84.93 | 848.00 | 848.0 | 840.0 |
| Avicel PH101 | 8.86 | 83.95 | 8.86 | 83.70 | 8.86 | 83.46 | 89.0 | 89.0 |
| Veegum F | 0.50 | 4.74 | 0.25 | 2.36 | 0.00 | 0.00 | — | — |
| Bentonite | — | — | — | — | — | — | 53.0 | NIL |
| Attapulgite | — | — | — | — | — | — | NIL | 53.0 |
| Explotab | 4.18 | 39.60 | 4.18 | 39.49 | 4.18 | 39.37 | 42.0 | 42.0 |
| Povidone K30 | 1.09 | 10.32 | 1.09 | 10.30 | 1.09 | 10.27 | 11.0 | 11.0 |
| Magnesium stearate | 0.94 | 8.91 | 0.94 | 8.88 | 0.94 | 8.85 | 9.1 | 9.1 |
| Tablet weight (mg) | 100.00 | 995.53 | 100.00 | 992.73 | 100.00 | 989.95 | 1052.1 | 1044.1 |

| Example Number | 32 mg/tablet | 33 mg/tablet |
|---|---|---|
| Acyclovir | 848.0 | 848.0 |
| Avicel PH 101 | 89.0 | 89.0 |
| Veegum F | 53.0 | 53.0 |
| low substituted hydroxypropyl cellulose LH-11 (LHPC LH-11) | 42.0 | NIL |
| low substituted hydroxypropyl methyl cellulose | NIL | 42.0 |
| Povidone K30 | 11.0 | 11.0 |
| Magnesium stearate | 9.4 | 9.4 |
| Film coat composite 1: Opadry | NIL | NIL |
| Film coat composite 2: Polyethylene glycol 8000 | NIL | NIL |
| Tablet weight (mg) | 1052.4 | 1052.4 |

Method of Preparation

The tablets described in Examples 1–33 above were prepared according to the following general method:

(a) A dry mixture was made of all components except Povidone/PVP K30, sodium docusate (if present) and magnesium stearate;

(b) The Povidone/PVP K30 and sodium docusate (if present) were dissolved in 50% aqueous alcohol to form a granulation solution;

(c) The granulation solution was added to the dry mixture to form granules;

(d) The wet granules were dried in a fluid bed dryer;

(e) The granules were then sifted through a 1000 μm diameter mesh sieve; and (f) The dried granules were blended with the magnesium stearate and compressed to form tablets.

Flavouring agents where present were added at blending step (f) above.

This general method is illustrated with respect to the following specific examples.

EXAMPLE 8

Uncoated Tablets (a) A dry mixture was made of all components except Povidone/PVP K30 and magnesium stearate using a Diosna P100 (high shear mixer—granulator) for 3 minutes.

(b) The Povidone/PVP K30 was dissolved in 50% aqueous alcohol to form a granulation solution.

(c) The granulation solution was added to an approximate quantity of 300 ml per kg dry weight to the dry mixture to form granules. Wet mixing was carried out for approximately 5 minutes.

(d) The wet granules were dried in an Aeromatic T3 fluid bed drier at a temperature of 70° C. for approximately 30 minutes. The moisture content of the granules was approximately 4%.

(e) The granules were then sifted through a 1000 μm diameter mesh sieve using a Jackson Crockatt No. 7 sifter.

(f) The dried granules were blended with the magnesium stearate using a collette mixer for approximately 10 minutes and compressed to form tablets using a Manesty D3 Rotary tablet press fitted with caplet shaped punches of approximately 19.3 mm length and 9.0 mm breadth. Tablets were compressed to a weight of 1052 mg±2%.

This granule can be used to make other strengths of acyclovir dispersible tablets, e.g. 200 mg and 400 mg, compressing the dried granules to a weight of respectively 263 mg and 526 mg, using round punches with diameters of respectively 8.6 mm and 11.0 mm.

EXAMPLE 9

Film Coated Tablets

Steps (a) to (f) described in Example 8 were repeated to form an uncoated tablet which was then film-coated by the following procedure.

The film-coating apparatus used was a Manesty Accellocota 10. The coating suspension was sprayed onto the tablet cores to a target weight increase of between 0.5–1.0% using suitable parameters of:

pan rotation speed (8.5 rpm)
spray (application rate (~20 g per min)
inlet temperature (~75° C.)
exhaust temperature (~53° C.)

A polish coat of PEG8000 was then applied to the film-coated tablets, to a further weight gain of 0.1–0.2%.

EXAMPLES 13 TO 15

In Example 13, Acyclovir, Avicel PH101, Sodium starch glycollate and Veegum F are dry mixed in a mixer. The mixture is then granulated after adding a sufficient volume of 50% aqueous alcohol (IMS). The resulting granules are dried, blended with the magnesium stearate and then compressed to form tablets.

EXAMPLE 14

The procedure described in Example 13 for the preparation of the granules and formation of the tablets is employed except that granulation of the dry mixture is effected with the Povidone in a 50% aqueous alcohol solution. Film coating of the resulting tablets can be optionally effected by treating the tablets with a dispersion of Opadry white dispersion in purified water and drying the coated tablets which are subsequently polished with a solution of polyethylene glycol 8000, USNF in 50% aqueous alcohol (IMS).

For Example 15, the procedure described in Example 13 for the preparation of the granules and formation of the tablets is employed except that granulation of the dry mixture was effected with the Povidone in a 50% aqueous alcohol solution.

The tablets prepared in accordance with the above Examples were then tested as follows.

Tablet Evaluation Methods

1. Average tablet weight. Twenty tablets were weighed on an analytical balance and the average tablet weight calculated.

2. Tablet breaking strength (kilo pond-kp). 5 tablets were individually tested using a Schleuniger crushing strength tester, and the average breaking strength calculated.

3. Friability (% loss). 10 tablets, accurately weighed, were subjected to 10 minutes friability testing using a Roche Friabilator. The tablets were dedusted, reweighed, and the weight loss due to the friability was calculated as a percentage of the initial weight.

4. Dispersion Disintegration time DT (BP 1988). 6 tablets were tested in accordance to the above-defined BP test (without discs) for dispersible tablets. This utilises water at a temperature of 19°–21° C.

5. Dispersion Quality. In accordance with the BP uniformity of dispersion test for dispersible tablets (BP 1988 Volume II page 895), two tablets were placed in 100 ml of water at 19°–21° C. and allowed to disperse. A smooth dispersion was produced which passed through a 710 μmesh sieve.

Granule Evaluation Methods

1. Loss on Drying (LOD). The residual moisture content of the granule (LOD) was determined on a 3–4 g sample using a Computrac moisture analyser set to 90° C. operated in accordance with the manufacturer's procedure.

2. Weight Median Diameter (WMD). A 10 g sample of granule was sifted for 2 minutes at suitable pulse and sift amplitudes in an Allen Bradley sonic sifter in accordance with manufacturer's instructions. Sieves of 710 μm, 500 μm, 355 μm, 250 μm, 150 μm, 106 μm and 53 μm were used. The WMD was calculated from the cumulative percentage undersize size distribution using a computer programme.

Acyclovir Granule and Tablet Evaluation Results

| Example Number | Actual Average Tablet Weight (mg) | Target Tablet Weight (mg) | Average Thickness (mm) | Average Breaking Strength (Kp) | Friability (%) | Disintegration time** First Tablet | Disintegration time** Last Tablet | Loss on Drying (% LOD) WMD (μm) | Weight median diameter | Tablet shape/ maximum diameter |
|---|---|---|---|---|---|---|---|---|---|---|
| 1 | — | 1248.0 | — | 11.0 | — | | 12'17" | 1.43 | — | Caplet* |
| 2 | — | 1048.0 | — | 11.6 | — | | 7'26" | 1.59 | — | Caplet |
| 3 | 1176 | 1163.2 | — | 10.7 | — | >10' | >10" | 2.28 | — | Round 14.0 mm |
| 4 | — | 1191.7 | — | 13.7 | — | | 4'50" | 1.18 | — | Round 14.0 mm |
| 5 | 1053 | 1055.5 | — | 15.0 | — | | 4'21" | 1.75 | 186 | Round 14.0 mm |
| 6 | 983 | 989.95 | 5.46 | 10.8 | 0.34 | 6'27" | 7'26" | 1.43 | 315 | Caplet |
| 7a | 1022 | 1048.4 | — | 7.2 | 2.74 | | 0'33" | 1.31 | 233 | Caplet |

**All dispersions passed through a 710 m sieve (BP uniformity of dispersion test)

| Example Number | Actual Average Tablet Weight (mg) | Target Tablet Weight (mg) | Average Thickness (mm) | Average Breaking Strength (Kp) | Friability (%) | Disintegration time** First Tablet | Disintegration time** Last Tablet | Loss on Drying (% LOD) WMD (μm) | Weight median diameter | Tablet shape/ maximum diameter |
|---|---|---|---|---|---|---|---|---|---|---|
| 7b | 1046 | 1048.4 | — | 12.8 | 0.47 | | 0'42" | 1.31 | 233 | Caplet |
| 7c | 1048 | 1048.4 | — | 17.1 | 0.19 | | 0'44" | 1.31 | 233 | Caplet |
| 8 (uncoated) | 1049 | 1052.4 | 7.0 | 14.6 | 0.18 | | 0'35" | 4.06 | 138 | Caplet |
| 9 (coated) | 1053 | 1062.4 | 6.99 | 16.1 | negligible | | 1'05" | 4.06 | 138 | Caplet |
| 10 | — | 1044.4 | — | 14.4 | 0.11 | — | 0'32" | 2.65 | 123 | Caplet |
| 11 | — | 1044.4 | — | 15.3 | 0.24 | — | 0'46" | 1.46 | 196 | Caplet |
| 12 | — | 1044.4 | — | 13.3 | 0.73 | — | 0'27" | 1.76 | 105 | Caplet |
| 13, 14, 15*** | | | | | | | | | | |
| 16 | 1051.24 | 1052.4 | 7.1 | 11.6 | 0.49 | 0'46" | 0'49" | 1.12 | 185 | Caplet |
| 17 | 1059.54 | 1052.4 | 7.0 | 11.8 | 0.46 | 0'28" | 0'30" | 2.18 | 125 | Caplet |
| 18 | 1060.79 | 1052.4 | 6.90 | 11.5 | 0.62 | 0'17" | 0'19" | 1.46 | 178 | Caplet |
| 19 | 1053.4 | 1052.4 | 6.70 | 11.6 | 0.71 | 0'19" | 0'24" | 2.00 | 73 | Caplet |
| 20 | 1057.6 | 1052.4 | 6.71 | 9.1 | 2.45 | 0'20" | 0'23" | 1.81 | 90 | Caplet |
| 21 | 1048.8 | 1052.4 | 7.24 | 11.5 | 0.85 | 2'18" | 2'59" | 1.15 | 341 | Caplet |
| 22 | 1743.9 | 1828.56 | 10.40 | 11.6 | 2.19 | 0'29" | 0'31" | 1.84 | 83 | Caplet |
| 23 | 1054.2 | 1052.4 | 6.90 | 11.5 | 0.09 | 0'43" | 0'51" | 1.84 | 157 | Caplet |
| 24 | 1059.1 | 1052.4 | 6.90 | 11.4 | 0.02 | 0'55" | 1'00" | 0.68 | 142 | Caplet |
| 25 | 1052.6 | 1052.4 | 6.70 | 11.9 | 0.09 | 1'30" | 1'42" | 1.59 | 118 | Caplet |
| 26a)# | 130.6 | 131.55 | 2.80 | 4.2 | 0.56 | 0'25" | 0'28" | 1.34 | 296 | 7.4 mm Round |
| 26b)# | 526.0 | 426.2 | 4.81 | 12.84 | 0.79 | 0'26" | 0'30" | 1.34 | 296 | 11.0 mm Round |
| 26c)# | 1216.5 | 1215.0 | 8.20 | 11.10 | 0.83 | 0'45" | 0'51" | 1.34 | 296 | Caplet |
| 27 | 125.7 | 124.4 | 3.68 | 3.68 | 0.71 | 0'33" | 0'39" | 1.21 | 334 | 7.4 mm Round |
| 28 | 124.7 | 124.1 | 2.78 | 3.55 | 0.65 | 0'44" | 0'47" | 1.90 | 332 | 7.4 mm Round |
| 29 | 982.9 | 989.95 | 5.46 | 10.8 | 0.34 | 6'27" | 7'26" | 1.43 | 315 | Caplet |
| 30 | 1041.2 | 1052.1 | — | 11.8 | — | 1'30" | 1'55" | 1.62 | 227 | Caplet |
| 31 | 1038.6 | 1044.1 | — | 16.6 | 1.59 | 1'50" | 2'10" | 1.96 | 150 | Caplet |

*Approximate dimensions of caplet were: 19.3 mm long, 9.0 mm wide, 7.0 mm thick.
**Disintegration times measured in accordance with BP test for dispersible tablets. All dispersions passed through a 710 m sieve (BP uniformity of dispersion)
Same granule formulation, but different compression weights giving approximately: a = 100 mg, b = 400 mg and c = 925 mg of acyclovir per tablet.
***Examples 13, 14 and 15 disintegrated in 0'30" to 1'30".

A particle size analysis was carried out on the dispersion of a tablet of Example 9 in accordance with the following method.

The particle size distribution was determined using a Malvern 2600 particle analyser as follows. The instrument was set to analyse particles in liquid with magnetic stirrer fitted. A 300 mm focal length lens was used.

1. Disperse tablet in 100 ml of de-ionised water.
2. Agitate solution for approximately 2 hours.
3. Filter or centrifuge solution to obtain liquor which should be saturated with all ingredients present in the tablet.
4. Disperse second tablet in 50 ml of saturated liquor allowing 3 minutes to fully disperse. Agitate vigorously and remove a sample of the dispersion within 5 minutes adding sufficient quantity to the Malvern PIL cell containing the liquor to obtain an observation value of 0.15–0.30. Analyse sample.

The particle size distribution was as follows:
Particle size: (as equivalent spherical volume)
<710 μm—100%
<300 μm—98.7%
<200 μm—86.7%
<130 μm—50% (median particle size)

We claim:

1. A water dispersible tablet having 200 to 800 mg of acyclovir, said tablet consisting essentially of: within the granules of the tablet, 65 to 95% w/w acyclovir; 0.25 to 5% w/w povidone; 0.5 to 30% w/w swellable clay; an additional excipient selected from the group consisting of 5 to 25% w/w hydroxyalkyl cellulostic disintegrating agent,1 to 8% w/w sodium starch glycollate and a mixture of the two; and within the tablet but not in the granules 0.25 to 2% w/w lubricant, to provide a tablet which is capable: (a) of dispersing in water to provide a dispersion which passes through a sieve screen with a mesh aperture of 710µ; (b) of disintegrating within three minutes when tested by the following apparatus and method in accordance with the test instructions for dispersible tablets of the British Pharmacopoeia, 1988,volume II, page 895; said apparatus consisting of: (i) a means for supporting six cylindrical glass tubes 75.0 to 80.0 long, 21.5 mm in internal diameter and with a wall thickness of about 2 mm; (ii) a cylindrical disc for each tube, each 20.55 to 20.85 mm in diameter and 9.35 to 9.65 thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disk in such a way that at the upper surface of the disc they are 9.5 mm wide and 2.55 mm deep and at the lower surface 1.6 mm square; (iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate, (iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 and 32 cycles per minute; (v) said assembly suspended in water at 19° to 21° C. held in a 1000-ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water, said method consisting of introducing one tablet into each of the six tubes, suspending said assembly in the beaker containing the water and operating the apparatus for a maximum period of three minutes so that all six of the tablets disperse.

2. A water dispersible tablet having 200 to 800 mg of acyclovir, said tablet consisting essentially of: within the granules of the tablet, 65 to 95% w/w acyclovir; 0.25 to 5% w/w povidone; 0.5 to 30% of a swellable clay selected from the group consisting of smectite, sepiolite or a mixture thereof; a cellulostic excipient selected from the group consisting of 5 to 25% w/w hydroxypropyl cellulose, hydroxypropylmethyl cellulose, 5 to 25% microcrystalline cellulose and a mixture thereof;1 to 8% w/w sodium starch glycollate; and within the tablet but not in the granules of the tablet 0.25 to 2% lubricant to provide a tablet which is capable of dispersing in water within a period of 3 minutes to provide a dispersion which is capable: (a) of dispersing in water to provide a dispersion which passes through a sieve screen with a mesh aperture of 710µ; (b) of disintegrating within three minutes when tested by the following apparatus and method in accordance with the test instructions for dispersible tablets of the British Pharmacopoeia, 1988, volume II, page 895; said apparatus consisting of: (i) a means for supporting six cylindrical glass tubes 75.0 to 80.0 long, 21.5 mm in internal diameter and with a wall thickness of about 2 mm; (ii) a cylindrical disc for each tube, each 20.55 to 20.85 mm in diameter and 9.35 to 9.65 thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disk in such a way that at the upper surface of the disc they are 9.5 mm wide and 2.55 mm deep and at the lower surface 1.6 mm square; (iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate; (iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 and 32 cycles per minute; (v) said assembly suspended in water at 19° to 21° C. held in a 1000-ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water, said method consisting of introducing one tablet into each of the six tubes, suspending said assembly in the beaker containing the water and operating the apparatus for a maximum period of three minutes so that all six of the tablets disperse.

3. A water dispersible tablet having 200 to 800 mg of acyclovir, said tablet consisting essentially of: within the granules of the tablet, 65 to 95% w/w acyclovir; 0.25 to 5% w/w povidone; 0.5 to 30% w/w of a swellable clay selected from the group consisting of smectite and sepiolite; 5 to 25% w/w of a cellulostic excipient selected from the group consisting of hydroxypropyl cellulose, hydroxypropylmethyl cellulose and a mixture thereof; and within the tablet but not in the granules of the tablet 0.25 to 2% w/w lubricant to provide a tablet which is capable: (a) of dispersing in water to provide a dispersion which passes through a sieve screen with a mesh aperture of 710µ; (b) of disintegrating within three minutes when tested by the following apparatus and method in accordance with the test instructions for dispersible tablets of the British Pharmacopoeia, 1988, volume II, page 895; said apparatus consisting of: (i) a means for supporting six cylindrical glass tubes 75.0 to 80.0 long, 21.5 mm in internal diameter and with a wall thickness of about 2 mm; (ii) a cylindrical disc for each tube, each 20.55 to 20.85 mm in diameter and 9.35 to 9.65 thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disk in such a way that at the upper surface of the disc they are 9.5 mm wide and 2.55 mm deep and at the lower surface 1.6 mm square; (iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate; (iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 and 32 cycles per minute; (v) said assembly suspended in water at 19° to 21° C. held in a 1000-ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water, said method consisting of introducing one tablet into each of the six tubes, suspending said assembly in the beaker containing the water and operating the apparatus for a maximum period of three minutes so that all six of the tablets disperse.

4. A tablet as claimed in claim 2 or 3 wherein there is about 800 mg of acyclovir present.

5. A tablet as claimed in claim 2 or 3 wherein the concentration of acyclovir is 75 to 85% w/w.

6. A tablet as claimed in claim 2 or 3 wherein the concentration of povidone is 0.3 to 2% w/w.

7. A tablet as claimed in claim 2 or 3 wherein the lubricant is magnesium stearate.

8. A tablet as claimed in claim 2 or 3 wherein the swellable clay is selected from the group consisting of monmorillonite, attapulgite and a mixture thereof.

9. A tablet as claimed in claim 8 wherein the monmorillonite are selected from the group consisting of magnesium aluminum silicate, bentonite and a mixture thereof.

10. A tablet as claimed in claim 1 or 2 wherein the concentration of swellable clay is 3 to 10% w/w.

11. A tablet as claimed in claim 3 wherein the concentration of said cellulostic excipient is 5 to 15% w/w.

12. A tablet as claimed in claim 1 or 2 wherein the concentration of sodium starch glycolate is 1 to 5% w/w.

13. A tablet as claimed in claim 3 further comprising 5 to 25% of microcrystalline cellulose.

14. A tablet as claimed in claim 2 or 3 wherein acyclovir is present in a hydrate form of ratio 3 acyclovir:2 water.

15. A water dispersible tablet having 200 to 800 mg of acyclovir and consisting essentially of: within the granules of the tablet, 65 to 95% w/w acyclovir; 0.25 to 5% w/w povidone; 0.5 to 30% w/w of a swellable clay; 5 to 25% w/w of hydroxypropylmethyl cellulose; and within the tablet but not in the granules of the tablet 0.25 to 2% w/w lubricant to provide a tablet which is capable: (a) of dispersing in water to provide a dispersion which passes through a sieve screen with a mesh aperture of 710μ; (b) of disintegrating within three minutes when tested by the following apparatus and method in accordance with the test instructions for dispersible tablets of the British Pharmacopoeia, 1988, volume II, page 895; said apparatus consisting of: (i) a means for supporting six cylindrical glass tubes 75.0 to 80.0 long, 21.5 mm in internal diameter and with a wall thickness of about 2 mm; (ii) a cylindrical disc for each tube, each 20.55 to 20.85 mm in diameter and 9.35 to 9.65 thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disk in such a way that at the upper surface of the disc they are 9.5 mm wide and 2.55 mm deep and at the lower surface 1.6 mm square; (iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate; (iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 and 32 cycles per minute; (v) said assembly suspended in water at 19° to 21° C. held in a 1000-ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water, said method consisting of introducing one tablet into each of the six tubes, suspending said assembly in the beaker containing the water and operating the apparatus for a maximum period of three minutes so that all six of the tablets disperse.

16. A tablet as claimed in claim 15 wherein the swellable clay is selected from the group consisting of attapulgite, bentonite, magnesium aluminum silicate and a mixture thereof.

17. A tablet as claimed in claim 15 or 16 further comprising 5 to 25% microcrystalline cellulose.

18. Granules for a water-dispersible tablet having 200 to 800 mg of acyclovir, the granules consisting essentially of 75 to 85% w/w acyclovir; 0.5 to 2% w/w povidone; 0.5 to 10% w/w of a swellable clay selected from the group consisting of magnesium aluminum stearate, bentonite, attapulgite and mixtures thereof; 5 to 15% w/w microcrystalline cellulose; and 2 to 6% w/w sodium starch glycollate.

19. A water-dispersible tablet having about 800 mg of acyclovir, said tablet consisting essentially of: within the granules of the tablet, 75 to 85% w/w acyclovir; 0.5 to 2% w/w povidone; 0.5 to 10% swellable clay selected from the group consisting of magnesium aluminium silicate, bentonite, attapulgite, and mixtures thereof; 5 to 15% w/w microcrystalline cellulose; 2 to 6% w/w sodium starch glycollate; and within the tablet but not in the granules of the tablet 0.25 to 1% w/w magnesium stearate.

20. A water dispersible tablet having about 800 mg of acyclovir, said tablet consisting essentially of: within the granules of the tablet, 75 to 85% w/w acyclovir; 0.5 to 2% w/w povidone; 0.5 to 10% swellable clay selected from the group consisting of magnesium aluminium silicate; bentonite, attapulgite and mixtures thereof; 5 to 15% w/w microcrystalline cellulose; 2 to 6% w/w sodium starch glycollate; and outside the granules of the tablet 0.25 to 1% w/w magnesium stearate.

21. A water dispersible tablet having 200 to 800 mg of acyclovir, said tablet consisting essentially of: within the granules of the tablet, 65 to 95% w/w acyclovir; 0.5 to 30% w/w swellable clay; an additional excipient selected from the group consisting of 5 to 25% w/w hydroxyalkyl cellulostic disintegrating agent, 1 to 8% w/w sodium starch glycollate and mixtures thereof; and within the tablet but not in the granules 0.25 to 2% w/w lubricant to provide a tablet which is capable: (a) of dispersing in water to provide a dispersion which passes through a sieve screen with a mesh aperture of 710μ; (b) of disintegrating within three minutes when tested by the following apparatus and method in accordance with the test instructions for dispersible tablets of the British Pharmacopoeia, 1988, volume II, page 895;

said apparatus consisting of: (i) a means for supporting six cylindrical glass tubes 75.0 to 80.0 long, 21.5 mm in internal diameter and with a wall thickness of about 2 mm; (ii) a cylindrical disc for each tube, each 20.55 to 20.85 mm in diameter and 9.35 to 9.65 thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disk in such a way that at the upper surface of the disc they are 9.5 mm wide and 2.55 mm deep and at the lower surface 1.6 mm square; (iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate; (iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 and 32 cycles per minute; (v) said assembly suspended in water at 19° to 21° C. held in a 1000-ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water, said method consisting of introducing one tablet into each of the six tubes, suspending said assembly in the beaker containing the water and operating the apparatus for a maximum period of three minutes so that all six of the tablets disperse.

22. A tablet as claimed in claim 1 or 2, which is further film-coated and wherein the dispersion time can be up to five minutes.

* * * * *